United States Patent [19]
Lew et al.

[11] 4,062,872
[45] Dec. 13, 1977

[54] PROCESS OF OXIDIZING HYDROCARBONS USING CATALYSTS WITH HIGH HEAT CONDUCTIVITY

[75] Inventors: Sandy Y. Lew, Libertyville, Ill.; Edward F. Conley, Holliston, Mass.

[73] Assignee: Brunswick Corporation, Skokie, Ill.

[21] Appl. No.: 689,248

[22] Filed: May 24, 1976

Related U.S. Application Data

[60] Continuation of Ser. No. 382,489, July 25, 1973, abandoned, which is a division of Ser. No. 133,391, April 12, 1971, Pat. No. 3,769,240.

[51] Int. Cl.$^2$ .................. C07D 307/89; C07B 3/00
[52] U.S. Cl. ........................... 260/346.4; 560/243; 260/385; 260/544 K; 260/599; 260/621 G; 260/654 A; 260/687 R; 526/352
[58] Field of Search .......................... 260/346.4, 687

[56] References Cited

U.S. PATENT DOCUMENTS 2,423,835   7/1947   Houdry .................... 260/680 R Primary Examiner—Henry R. Jiles
Assistant Examiner—Bernard Dentz
Attorney, Agent, or Firm—John G. Heimovics

[57] ABSTRACT

An improved catalyst structure for use in catalytic processes, consisting of a powdered catalyst, carrier, and metal fiber thoroughly mixed to assure a permanent uniform distribution of the metal fiber, the catalyst-metal fiber mixture then pressed into any desired shape for its intended use. The permanent uniform dispersion of metal fibers results in a catalyst structure having increased thermal conductivity and more uniform porosity, the improved heat transfer characteristics increasing selectivity and minimizing temperature gradients in the catalytic structure thereby assuring constant reactor temperature and imparting stability, improved yield and temperature control in highly exothermic and endothermic catalytic reactions.

4 Claims, No Drawings

PROCESS OF OXIDIZING HYDROCARBONS USING CATALYSTS WITH HIGH HEAT CONDUCTIVITY

CROSS REFERENCE TO CO-PENDING APPLICATION

This is a continuation of copending application Ser. No. 382,489 filed July 25, 1973, now abandoned, which is a divisional application of co-pending application Ser. No. 133,391, filed Apr. 12, 1971, now U.S. Pat. No. 3,769,240.

FIELD OF THE INVENTION

This invention relates to a simple stable catalyst structure for use in catalytic reactions, to a method of preparing such a catalyst, and to improved processes employing the catalytic structure.

This invention also relates to an improved catalytic structure wherein a stable uniform distribution of metal fibers in the catalyst structure is easily achieveable and maintainable in powderized form prior to any compacting operation, and wherein stability in the catalyst reactor temperature is achieved by the mixture of catalyst and metal fiber.

In some conventional catalytic processes using solid particulate oxidation catalysts, the reactants are passed through a fixed bed of porous oxidation catalyst particles or pellets. If the catalytic reaction is hydrogenation such as that involving the oxidation of hydrocarbons, the reaction can be highly exothermic which causes problems with heat transfer and temperature control within the catalyst bed. The heat evolved from these exothermic reactions causes the formation of localized hot spots, and gross temperature gradients throughout the catalyst structure. The resulting temperatures may be high enough to cause sintering of the catalyst structure (fusion of the catalyst pellets) thereby effecting a loss in catalyst surface area and catalyst activity. Furthermore, unless the heat is dissipated substantially uniformly through the catalyst bed or away from the reaction area entirely these localized hot spots and temperature gradients within the catalyst bed will cause a decrease in yield and selectivity of the reactant product. Accordingly, in order to achieve maximum yield and selectivity of the reactant product and in making the catalytic reaction economic, it is necessary to keep the catalytic reaction within a specified temperature range by accurate temperature control in a simple and economical way.

Several definitions used in the specifications should be defined. Catalyst activity is the effectiveness of the catalyst structure to convert the reactants to the desired reactant product. The selectivity of the catalyst is the purity of the reactant product determined by the decrease in amount of contaimination by other products. The catalyst is the active agent used in a particular catalytic process. The reactant product is the material produced. The yield of the reactant product is the percent reactant product return based on the weight of reactant introduced in the catalytic reactor. The carrier for the catalyst is the carrier as conventionally employed in supporting the catalyst used and usually provides a large surface area on which the active catalyst can be dispersed.

Prior Art

Some techniques for increasing yield and selectivity in catalytic processes have been an attempt to increase the surface area of the catalyst by dispersing the catalyst on a carrier. Catalyst surface area has the effect of increasing the catalyst activity at lower reactor temperatures. Increased catalytic activity leads to greater operating loads while still producing a good yield of product and selectivity (purity of product), with a corresponding increase in heat transfer problems within the catalyst bed. Some of these methods are described in U.S. Pat. Nos. 2,973,371; 3,410,651; 3,240,698; 3,362,783; and 3,231,520.

The four latter patents mentioned disclose the use of a metal substrate that is given an adherent coat of alumina, calcining this alumina, and then impregnating the alumina with the desired catalyst. The problems with these methods are that the steps involved in developing these catalytic structures are complicated, difficult, time consuming and costly.

The prior art has also disclosed the use of inert and inactive materials in gross proportions to dilute the catalyst to eliminate localized hot spots in highly exothermic catalytic reactions. Although this method can approach isothermal reactor conditions, it results in a purity of final product much lower than the maximum possible and increases the cost of productivity. There have also been other attempts to make catalysts having a varying dilution of inert or inactive materials dispersed throughout the catalytic bed, in order to permit higher operation temperatures in certain portions of the reactor, in order to increase yield, see "Catalyst Dilution - A Means of Temperature Control in Packed Tubular Reactors", by A. D. Caldwell and P. H. Claderbank, *British Chemical Engineering*, September, 1969, Vol. 14, No. 9. However, all these approaches have required specially designed reactors, materials, and equipment which substantially increases production costs.

It has also been generally disclosed to use short thick non-uniform lengths of wire, rod, lumps, pieces of metal or other suitable heat conductive material distributed at random throughout the catalyst bed to facilitate heat transfer and permit temperature control of the catalyst reactor. Some of these are described in U.S. Pat. Nos. 2,491,057; 3,240,698; and 3,231,520. However, these catalyst structures contemplated the use of relatively large size wires or rods as compared to the particle size of the catalyst. Accordingly, all have the inherent problem of having these pieces of metal only temporarily dispersed within the catalyst structure, unless the metal wire-catalyst structure was bonded together by some process. These catalyst structures then, because of the relatively large metal masses incorporated therein, had a tendency to clot, flocculate, agglomerate, or settle out of the structure. These factors necessarily limited the amount of metal wire that could be incorporated effectively, and also limited the particle size of the catalyst which helped support and keep the wires uniformly dispersed. Accordingly, the prior art only produced a temporary dispersion of large metal masses in a powder catalyst mixture prior to this catalyst mixture being given mechanical integrity by some conventional compacting or pelletizing process. If this powder catalyst mixture with metal masses was transported in the uncompacted state, the metal masses would surely settle out of the catalyst mixture when subjected to a minimal amount of vibration. Therefore, it was necessary, in the prior art, to compact the powder catalyst metal mass mixture very soon after incorporating these large metal masses, before any settling out of the metal masses occurred.

Another problem in the prior art is with the conventional carriers used to support the catalyst bed. The carriers conventionally used provide a large surface area to increase the effectiveness and activity of the catalyst, and usually have a low thermal conductivity. Accordingly, the carrier limits the rate at which heat may be dissipated from the catalyst and prevents the rapid removal of heat evolved during the catalytic reaction in order to avoid formation of localized hot spots.

Finally, with many catalytic processes it is necessary to use a fluidized bed to eliminate localized hot spots and high temperature gradients. The best conventional methods and catalysts for the oxidation of hydrocarbons are only capable of producing yields between 80 – 90%. In some cases, it is further necessary to go through several partial hydrocarbon oxidation steps, since a slight rise in temperature could approach a complete uncontrollable exothermic reaction.

SUMMARY OF THE INVENTION

It is accordingly a general object of this invention to obviate the difficulties and problems in the prior art and to provide for an improved catalyst structure for catalytic reactions, and in particular the oxidation of fluid hydrocarbons (in a gas, vapor, or liquid state), wherein a simple catalytic structure having a high thermal conductivity is provided having metal fibers or filaments uniformly associated with the catalyst and carrier in a permanent and uniform dispersive relationship, the fibers uniformly dissipating and minimizing high fluctuations in temperature in the catalyst bed that occurs in highly exothermic catalytic reactions. The metal fibers permit the rapid removal of the heat developed during the catalytic reaction in such a way that uniform temperature distribution and thermal conductance in the bed is achieved, thereby eliminating localized hot spots and imparting temperature stability and control to the reactor. The results are increases in yield and selectivity of the reactant product to levels not heretobefore achievable by other methods or catalyst structures.

Another object of the present invention provides for an improved catalyst structure having a permanently stable uniform dispersion of metal fibers that permits continued and uninterrupted catalyst structure effectiveness over extended periods of time.

A feature of the present invention is to provide for a simple method of preparing the catalyst structure of the present invention for selective catalytic reactions.

Another feature of the present invention provides for an improved catalytic structure which may eliminate the necessity of having to use a fluidized bed, and which increases the yield and selectivity of the reactant product to a degree not heretobefore possible by conventional methods. With the yield approximating a total conversion of reactant to reactant product (yields of 99% reactant product possible), there is a corresponding reduction in the cost of the hydrocarbon oxidation process and the quantity of catalyst required as compared to conventional methods and catalysts.

Still another feature of the present invention resides in the provision of a powder catalyst mixture having mechanical integrity formed by conventional compacting means into a catalyst structure of any desired shape depending upon its intended use.

The novel features which are believed to be characteristic of this invention are set forth with particularity in the appended claims. The invention itself, however, together with further objects, features, and advantages thereof, will best be understood by reference to the following description.

DESCRIPTION OF THE PREFERRED EMBODIMENT

In general, the catalyst structure of the present invention consists of a finely powdered oxidation catalyst mixed and blended thoroughly with metal fibers or filaments, this mixture ground, pulverized, or ball milled to assure uniform distribution and dispersion of the metal fiber. The metal filaments contemplated to be used in the catalyst structure of the present invention should have a diameter of one mil or less, preferably a diameter around 12 microns, and an aspect ratio (length/diameter) between 10 and 400. These small diameter fibers have only recently become obtainable by new processes such as those described in U.S. Pat. Nos. 3,379,000; 3,505,039; and 3,540,114. This fiber size permits them to be uniformly mixed in a dry state by pulverization or other similar methods, such that they are broken up into discrete fibers that will not settle out of the catalyst-metal fiber mixture. Accordingly, this physical characteristic will define a self-supporting catalyst structure having a plurality of metal fibers permanently and uniformly distributed therein. Having these minute dimensions, the metal fibers exhibit characteristics different from that of large diameter wires or metal masses as disclosed in the prior art, when incorporated in a solid-solid particulate dispersion.

It should be noted that when the powder catalyst structure of the present invention is compacted or pressed into a pellet or particle for use in a fixed bed catalytic reactor, the size of the pellet to a great degree will determine what length of filament is the most economical to use, since both discrete and continuous filaments will impart equivalent thermal conductive properties to the catalyst structure. Although the filament diameter should be 1 mil or less, with a preferred diameter around 12 microns, it is easier to incorporate short length, discrete fibers or filaments in small size pellets, whereas it may be easier to incorporate continuous length filaments in larger size pellets. Accordingly, no preferable range of filament aspect ratio can be given for a particular size pellet and the economics of incorporating the filament in that size pellet.

This uniform distribution of metal fibers will be free from parallel clumps or bundles of fibers, although such fibers, because of the high aspect ratios involved, will contact one another at various angles. The great surface area inherent with metal fibers of this size not only helps keep the fibers permanently dispersed (since it is believed that they readily conform to the surface characteristics of the finely powderized catalyst and develop a fiber-catalyst powder surface adhesion), but also assures exceptional conductivity of the heat of the catalytic reaction. The relationship between the particle size of the catalyst and carrier as pulverized, and the diameter and aspect ratio of the metal fiber, will determine the permanency of the metal fiber dispersion and the extent to which the catalyst structure will remain stable and uniform.

The method of preparing this catalyst structure also contributes to the great uniformity and stability of the metal fiber dispersion since pulverization in a dry state precludes any tendency of the metal fibers to clot, agglomerate, or bundle.

As stated earlier, the prior art powder catalyst structures incorporating large metal masses, could not be transported over long distances, unless compacted in a pellet form. This was so since the vibration normally encountered during transportation would cause the metal masses to settle out of the mixture. With the structure of the present invention, however, it is possible to maintain a stable uniform dispersion of metal fibers in a powder catalyst structure without such structure having to be pelletized or compacted. This permits transporting the catalyst structure over long distances without the metal fibers settling out of the mixture when subject to vibration. This permanency of uniform fiber dispersion, permits the catalyst-fiber structure to be economically produced and shipped in powder form (heretobefore not possible), thereby permitting the user of the catalyst structure to pelletize or compact the mixture in any desired shape or size according to their intended use.

After the catalyst-metal fiber mixture has been pulverized, it may then be pressed into any desired shape depending on its intended use. The uniformly dispersed metal filaments impart a high thermal conductivity to the catalyst structure thereby eliminating temperature gradients and localized hot spots, by the rapid absorption and conduction of the heat of reaction, substantially uniformly through the catalyst structure or to a point of lower heat content. Therefore, in accordance with the present invention, it is possible to control the temperature of the catalytic reaction with much greater accuracy and impart stability to the catalytic reactor. The catalysts that can be employed are those used in the oxidation of hydrocarbons, some of which are those used for the manufacture of: phthalic anhydride; anthroquinone; phenol; benzaldehyde; phosgene; vinyl acetate; maleic anhydride; polyethylene; and vinyl chloride.

The catalyst structure comprises three parts, the particular catalyst used as the active agent in the catalytic process, a carrier for the catalyst, and a plurality of discrete metal filaments or fibers. The particular form in which the catalyst or oxidation catalyst normally exists is not important, since the method of forming the catalyst structure of the present invention results in powderizing the catalyst. The catalyst may be materials or compounds of such elements from Groups I through VIII of the Periodic Table, and, for example, oxides of the following metals: copper; bismuth; tin; silver; zinc; chromium; vanadium; manganese; cobalt; tungsten; nickel; platinium; and iron; and combinations thereof.

The carrier used may be that conventionally obtainable with catalysts, and a specific type is not critical to the operability of this invention. However, it is generally known that the type of carrier may affect the catalytic properties of the finished catalyst, and the adsorption and desorption processes which accompany a heterogeneous catalytic reaction. Also some choice must be exercised with catalyst employing the transition metals or metal oxides, these catalyst having extraordinary dependence on the type of carrier used.

The carriers in commercially available catalysts used in the oxidation of hydrocarbons determine the optimum operating temperature of the reaction. This is so since the carrier material acts as an inhibitor in helping to prevent the severity of the reaction. The exact composition of the carrier plus the active portion of catalyst to carrier will determine the operating conditions of the catalytic reaction.

The metal fibers, filaments, or elongated elements used in this invention are not limited to any particular metal. Although any metal be used, it is preferable that the metals have a high thermal conductivity and a high resistance to oxidation at elevated temperatures to assure a uniform continual heat conduction not lowered by a possible oxide coating developed on the fiber during the catalytic reaction. The heat transfer characteristics of the metal fiber will vary with changes in the fiber surface, diameter, aspect ratio, and distance between adjacent fibers. Accordingly, the optimum operating conditions for the particular catalyst used in the catalytic structure of the present invention, will necessitate selection of metal filament on the basis of its diameter and length, resistance to oxidation at elevated temperatures, thermal conductivity, and its compatibility with respect to poisoning the catalyst (i.e., reducing the catalyst activity).

The considerations in selecting the diameter and length of the filament must include the filament's ability to freely disperse through the powdered catalyst without agglomeration, and use of a filament with the lowest practical diameter to reduce the overall cost of the catalytic structure. The smallest diameter fiber practical also assures permanency and stability in the uniform dispersion of fibers. Since catalytic reactions involving the oxidation of hydrocarbons involve heat transfer by both heat conduction within the catalyst structure and convection of heat out of the catalytic reactor by the reactant product, the oxidation of hydrocarbons within a catalyst having no metal fibers dispersed therethrough, results in a great amount of heat transferred by convection of the reactant products as compared to a reduced amount of heat transfered by convection of the reactant products within a catalyst structure containing a dispersion of fine fibers according to the present invention. Although the percentage of weight of metal fiber in the catalyst structure may be low (2 – 25% being the preferred range, as will be described later), the minute size of the fiber results in a correspondingly large number of filaments (in the millions per cubic inch) incorporated as part of the catalyst structure. It is believed that this ability to incorporate a great number of fine fibers (not heretobefore possible in the prior art) in a catalyst structure, helps to decrease the amount of heat transfered by convection of the reactant product and causes a corresponding increase in the amount of heat transfered by conduction uniformly through the catalyst structure. This is true whenever the catalytic reaction involves a fluid reactant flow, through a catalytic reactor. The effect assures that the heat of the catalytic reaction can be more uniformly and effeciently distributed throughout the catalyst structure, and uniformly dissipated out or uniformly absorbed within (depending whether their reaction is exothermic or endothermic, respectively) the catalyst structure.

Since the amount and number of metal fibers incorporated in the catalyst structure is dependent on a number of factors including fiber diameter, density, and aspect ratio as compared to the catalyst particle size and density, it is believed these factors determine to a great extent the ability of the fiber to be compatible with the catalyst particles in order to define a self-supporting homogeneous catalytic structure.

The metal fibers in the catalyst structure of the present invention, will be evenly distributed in all directions with no particular orientation. The fiber-catalyst contact points are surface oriented and not fiber-fiber point contact oriented as in the prior art catalytic structures.

In general, catalysts typically used in the oxidation of hydrocarbons are a finely divided powder supported by a high surface area carrier. According to the present invention, the commercially available catalyst is ground or pulverized as in a ball mill to a fine mesh powder. Then, fine diameter metal filaments 1 mil or less, are added to the powder in the desired proportion and then throughly mixed for a sufficient period of time until a uniform and permanent distribution of filaments is achieved. The powder-filament mixture can then be given mechanical integrity by being pelletized or compacted into any desired shape by conventional means.

As stated before, many of the catalytic reactions in the oxidation of hydrocarbons are highly exothermic or endothermic in which temperature control is very difficult. Accordingly, it is necessary then to dissipate the heat developed or add heat to the reaction to maintain a long life catalyst at optimum operating conditions within specified temperature ranges. Temperatures over or under the specified temperature range for the particular catalytic reaction will result in over or under oxidation of the reactant yielding undesirable products with a reduction in yield and selectivity of the reactant product.

In the use of the catalytic structures made according to the present invention, a marked stability of reactor operating temperature is achieved, thereby permitting precise control of the reactor temperature for optimum yield and selectivity of the reactant product. However, in a number of repeated uses of the same catalyst structure, containing stainless steel filaments and subjected to a cyclic temperature change, wherein the catalyst structure temperature was brought down to room temperature from its elevated operating temperature, it was noted that there was a small diminishment of control over the stability of the reactor temperature, and metallographic examination of the stainless steel filaments indicated that the surface of the stainless steel filaments had become oxidized. It is believed that this oxidation of the surface of the metal fiber is the cause for the diminishment in control of the reactor temperature since the surface oxide coating will reduce the thermal conductivity of the filament and therefore its ability to uniformly dissipate and disperse the heat away from and through the catalyst structure. Accordingly, it is apparent that in order to obtain the optimum yield, selectivity, and life of catalyst, the material used for the metal filaments must be carefully selected on the basis of those factors described previously. It is further desirable, for economic reasons, to incorporate the least amount of filament that will permit optimum operating conditions. Table I shows a range of catalyst structures incorporating stainless steel metal filaments 1 mil diameter by 0.270 inches long, and it is seen that the economic range of operation lies somewhere between 2–25% by weight of filament. Although incorporation of filament up to 25% by weight does not poison the catalyst, there is no gain in yield or selectivity and consequently no apparent economic advantage to doing so.

TABLE I

| Catalyst | Vanadium Oxide Catalyst (V$_2$O$_5$) | | | |
|---|---|---|---|---|
| | Air Flow Rate (cc/min) | Reactor Temp. ° C | Yield (wt.%) | Product |
| V$_2$O$_5$ | 900 | 360 | 48 | Phthalic Anhydride + 1-4 Napthoquinone |
| V$_2$O$_5$ + 2 wt% 304 ss fiber | 900 | 360 | 70 | Phthalic Anhydride + 1-4 Napthoquinone |
| V$_2$O$_5$ + 10 wt% 304 ss fiber | 900 | 360 | 99 | Phthalic Anhydride + 1-4 Napthoquinone |
| V$_2$O$_5$ + 25 wt% 304 ss fiber | 900 | 360 | 98 | Phthalic Anhydride + 1-4 Napthoquinone |

In the conversion of reactants to reactant products using a catalyst structure made according to this invention, the selectivity and activity of the catalyst is critically dependent on the operating temperature range which will determine whether under or over oxidation of the reactant will occur. Due to some complete combustion of reactant in some catalytic processes and the rapid rate of reaction, the total heat liberated may be as high as 10,000 BTU per pound of reactant creating an obvious heat exchange problem. With the catalysts containing fibers as in the examples noted in Table I, the reactor had a marked stability in temperature as compared to as received commercially available vanadia catalysts, and from this it is concluded the temperature control is effected by the fiber incorporation.

A typical example of hydrocarbon oxidation processes, is the process for making phthalic anhydride. This catalytic reaction is highly exothermic in which temperature control of the reactor is difficult to achieve. The catalyst used in this invention is vanadium pentoxide manufactured by Grace Chemical Company, grade 903 vanadia catalyst ⅛ inches × ⅛ inches pills. This finely divided powder is supported by a high surface area silica gel substrate, with a vanadia content of approximately 6% by weight. A heat treatment assures the vanadium has been raised to its highest oxidation state and that all the remaining binder material, which is used for the manufacture of the vanadia catalyst pills, is burned off.

The vanadia reactor considered of the activated fiber incorporated catalyst, through which an air/napthalene charge, in a ratio of 15:1 was passed at a flowrate of 900 cc/min. and a pressure of 10 p.s.i. The reactor was easily maintained at 360° C ± 10° C, with the napthalene being converted to phthalic anhydride. The phthalic anhydride vapor was then passed through a cold trap maintained at −20° C and there solidified according to conventional methods. The remaining gaseous effluent was combined with ethyl ether with further phthalic anhydride subsequently recyrstalized from the solution.

The optimum yield of phthalic anyhdride is produced in the temperature range of 360° ± 10° C, with temperatures over or under this range resulting in over or under oxidation, respectively, of the napthalene yielding undesirable products such as 1-4 napthoquinone, phthalic acid, maleic acid, succinic acid, etc. With a vanadium pentoxide catalyst structure made according to the present invention, a yield of 99% phthalic anhydride was obtained with only a slight trace of 1-4 napthoquinone. Throughout this reaction, the temperature of the catalyst structure was easily maintainable within the optimum operating temperature range of 360° C ± 10° C.

Table II shows the effect on yield and selectivity of temperatures above and below 360° C. The catalysts incorporating fibers according to the present invention, at temperatures above 360° C, all had approximately a 10% 1-4 napthoquinone contamination, which is a contaminating product due to incomplete oxidation. Also it was found that at temperature below 360° C, there was a gradual increase in yield of the reactant product, phthalic anhydride up to a maximum at 360° C, and a gradual decrease in yield of reactant product at temperatures above 360° C. This was also found to be true using as received vanadium pentoxide ($V_2O_5$), which at temperatures below 360° C. Showed a substantial amount of unreacted napthalene present indicating under oxidation. Accordingly, it can be concluded then, that for fiber incorporated vanadium catalysts as well as the as received vanadia catalyst, 360° C is the optimum reactor temperature.

Table II also shows the high degree of selectivity achieveable by the catalyst structure of the present invention. The catalyst incorporating a 25 weight percent of 304 stainless steel fiber at 310° C yielded 100% 1-4 napthoquinone whereas the identical catalyst at 360° C (a change of only 50° C) yielded 98% phthalic anhydride. This further indicates the great degree of selectivity of the catalyst structure of the present invention, selectivity of this degree not possible with prior art catalyst structures.

TABLE II

Optimum Reactor Temperature for Vanadium Oxide Catalyst

| Catalyst | Air Flow Rate (cc/min) | Reactor Temp. ° C | Yield (wt.%) | Product |
|---|---|---|---|---|
| $V_2O_5$ | 650 | 250 | 5 | Phthalic Anhydride + remainder unreacted napthalene |
| $V_2O_5$ | 650 | 300 | 9 | Phthalic Anhydride + remainder unreacted napthalene |
| $V_2O_5$ | 650 | 360 | 39 | Phthalic Anhydride + 1-4 napthoquinone |
| $V_2O_5$ + 10 wt% 304 ss fiber | 900 | 360 | 99 | Phthalic Anhydride + a trace of 1-4 napthoquinone |
| $V_2O_5$ + 10 wt% 304 ss fiber | 900 | 410 | 83 | Phthalic Anhydride + 10% 1-4 napthoquinone |
| $V_2O_5$ + 10 wt% 304 ss fiber | 900 | 450 | 85 | Phthalic Anhydride + 10% 1-4 napthoquinone |
| $V_2O_5$ + 25 wt% 304 ss fiber | 900 | 310 | 100 | 1-4 Napthoquinone |
| $V_2O_5$ + 25% 304 ss fiber | 900 | 360 | 98 | Phthalic Anhydride + a trace of 1-4 Napthoquinone |

While we have shown and described specific embodiments of the present invention, it will, of course, be understood that other modifications and alternative construction may be used without departing from the true spirit and scope of this invention. We therefore intend by the appended claims to cover all such modifications and alternative constructions as fall within their true spirit and scope.

What we intend to claim and secure by Letters Patent of the United States is:

1. In a method for the catalytic oxidation of a fluid hydrocarbon material which comprises the steps of:
   1. contacting the hydrocarbon with a catalyst, the catalytic material being an oxide of a metal selected from Group I through Group VIII of the Periodic Table and (2) recovering the product: the improvement comprising using as the catalyst a plurality of pellets comprised of:
      a compacted powdered catalytic matrix material and
      a plurality of textile metal fibers uniformly dispersed in a random orientation throughout the matrix, the fibers being free of a catalytic coating and having a diameter less than 1 mil and comprising from about 2% to about 25% of the pellet weight.

2. A method according to claim 1 wherein the catalytic material is an oxide of a metal selected from the group consisting of copper, silver, zinc, tin, bismuth, vanadium, chromium, molybdenum, manganese, cobalt and iron.

3. In a hydrocarbon oxidation process comprising the steps of
   a. providing a bed of catalyst particles, each containing compatibly inert, catalytic coating free, finely divided, heat conducting, metallic materials in a uniform, isotropic distribution throughout a catalytic mass, the catalyst being a metal oxide selected from Groups I through VIII of the Periodic Table;
   b. passing reactants including a fluid hydrocarbon through the bed;
   c. maintaining the bed at a temperature high enough to produce, in conjunction with the catalyst particles, oxidation of said fluid hydrocarbon; and
   d. recovering the product; the improvement step comprising:
      providing the metallic materials in the form of a plurality of textile metal fibers having a diameter of under 1 mil and an aspect ratio of from 10 to 400; whereby the metallic materials are permanently dispersed in uniform distribution without parallel clumps, assuring exceptional heat conductivity in the bed.

4. A method of producing phthalic anhydride which comprises the steps of:

1. providing a bed of catalytic pellets, each comprised of:
    a compacted powdered catalytic matrix material, the catalytic material consisting of a mixture of about 6% by weight of calcinated activated vanadium oxide and about 94% by weight silica gel; and,
    a plurality of textile metal fibers uniformly dispersed in a random orientation throughout the matrix, the fibers being free of a catalytic coating and having a diameter of less than 1 mil and comprising from about 2% to about 25% of the pellet weight;
2. heating and maintaining the bed of catalytic pellets to a temperature within the range of about 350° – 370° C; and
3. passing a mixture of napthalene vapor and air in contact with the bed of heated catalytic pellets to produce phthalic anhydride.

* * * * *